United States Patent [19]

Urry et al.

[11] Patent Number: 4,870,055

[45] Date of Patent: Sep. 26, 1989

[54] SEGMENTED POLYPEPTIDE BIOELASTOMERS TO MODULATE ELASTIC MODULUS

[75] Inventors: Dan W. Urry, Vestavia Hills; U. Prasad Kari, Birmingham, both of Ala.

[73] Assignee: University of Alabama at Birmingham, Birmingham, Ala.

[21] Appl. No.: 180,677

[22] Filed: Apr. 8, 1988

Related U.S. Application Data

[63] Continuation of Ser. No. 853,212, Apr. 17, 1986, abandoned.

[51] Int. Cl.$^4$ .................... A61K 37/02; C07K 7/10
[52] U.S. Cl. ............................... 514/12; 514/13; 514/17; 514/18; 530/324; 530/326; 530/329; 530/330; 530/345; 530/350; 530/402; 530/849; 623/11; 623/66
[58] Field of Search ............... 530/350, 849, 324, 326, 530/329, 330, 402, 345; 623/11, 66; 514/12, 13, 17, 18

[56] References Cited

U.S. PATENT DOCUMENTS

| | | | |
|---|---|---|---|
| 4,474,851 | 10/1984 | Urry | 428/374 |
| 4,500,700 | 2/1985 | Urry | 428/35 |
| 4,589,882 | 5/1986 | Urry | 514/12 |
| 4,605,413 | 8/1986 | Urry | 424/422 |
| 4,693,718 | 9/1987 | Urry | 530/328 |

OTHER PUBLICATIONS

Sandberg et al., "Pathologie Biologie" vol. 33 (4) pp. 266–274 (4/1985).

*Primary Examiner*—Delbert R. Phillips
*Assistant Examiner*—Christina Chan
*Attorney, Agent, or Firm*—Oblon, Spivak, McClelland, Maier & Neustadt

[57] ABSTRACT

A method of increasing the modulus of elasticity of a biopolymer is disclosed, which comprises incorporating a hexameric unit of the formula $$-X-(APGVGV)_n-Y-$$

wherein
A is a peptide-forming residue of L-alanine;
P is a peptide-forming residue of L-proline;
G is a peptide-forming residue of glycine;
V is a peptide-forming residue of L-valine;
X is PGVGV, GVGV, VGV, GV, V, or a covalent bond;
Y is APGVG, APGV, APG, AP, A, or a covalent bond; and
n is an integer from 2 to 200, wherein said hexameric unit comprises at least 18 amino acid residues, into an elastomeric polypeptide chain.

14 Claims, No Drawings

SEGMENTED POLYPEPTIDE BIOELASTOMERS TO MODULATE ELASTIC MODULUS

BACKGROUND OF THE INVENTION

The government has rights in this invention as a result of the work described herein being supported in part by the National Institutes of Health under grant No. HL-29578.

This application is a continuation of application Ser. No. 06/853,212 filed on Apr. 17, 1986, now abandoned.

FIELD OF THE INVENTION

This invention relates to bioelastomers, particularly to bioelastomers which can be used as replacements for elastin, and to methods of modifying the elasticity and tensile strength of these bioelastomers.

DESCRIPTION OF THE BACKGROUND

Tissue resulting from wound repair, commonly known as scar tissue, is visibly distinct from normal tissue and is generally conceded to be deficient in the elastic fiber component normally present in skin, blood vessels, and related tissue. Previous investigations into the structure of elastic fibers present in blood vessel walls and other elastic materials, such as ligaments, present in humans and animals, has given some insight into the structure of these elastic fibers. The connective tissue of vascular walls is formed from two principal types of protein. Collagen, the principal proteinaceous component of connective tissue, forms the strength-giving structure. In the vascular wall, and particularly in its internal elastic lamina, collagen is associated with natural elastic fibers formed from a different protein, known as tropoelastin. In the relaxed vascular wall, the collagen fibers tend to be folded or crimped, and the elastic fibers are in their retracted state. On distension or stretching, the elastic fibers stretch out, and, as their extension limit is approached, the collagen fibers come into tension to bear the load. As the load diminishes, the elastic fibers draw the wall back to its original dimensions and the collagen fibers back into their folded state. In a synthetic vascular material of the types currently available, such as Dacron, the weave can be viewed as providing the structural analogue of folded collagen, but there is no true elastomeric component.

The central portion of the elastic fibers of vascular wall, skin, lung and ligament is derived from a single protein called tropoelastin. Polypeptide sequences of tropoelastin from vascular wall have been shown by Sandberg and colleagues to contain a repeat hexapeptide (Ala-Pro-Gly-Val-Gly-Val)$_n$, a repeat pentapeptide (Val-Pro-Gly-Val-Gly)$_n$, and a repeat tetrapeptide (Val-Pro-Gly-Gly)$_n$ where Ala, Pro, Val and Gly respectively represent alanine, proline, valine and glycine amino acid residues. Peptide representations in this application conform to the standard practice of writing the NH$_2$-terminal amino acid residue at the left of the formula and the CO$_2$H-terminal amino acid residue at the right. Likewise, the amino acid sequence in the vicinity of natural crosslinks of tropoelastin is known, as disclosed in Gray et al., Nature, 246, 461–466 (1973). A high polymer of the hexapeptide has been synthesized, whereby it forms cellophane-like sheets. The hexapeptide was therefore thought to fill a structural role in the natural material. Synthetic high polymers of the pentapeptide and of the tetrapeptide, on the other hand, are elastomeric when cross-linked and appear to contribute to the functional role of the elastic fiber. For example, the chemically cross-linked polypentapeptide can, depending on its water content and degree of crosslinking, exhibit the same elastic modulus as native aortic elastin.

A synthetic polypentapeptide based on the pentapeptide sequence discussed above was disclosed and claimed in U.S. Pat. No. 4,187,852 to Urry and Okamoto. A composite bioelastic material based on an elastic polypentapeptide or polytetrapeptide and a strength-giving fiber was disclosed and claimed in U.S. Pat. No. 4,474,851 to Urry. A bioelastic material having an increased modulus of elasticity formed by replacing the third amino acid in a polypentapeptide with an amino acid of opposite chirality was disclosed and claimed in U.S. Pat. No. 4,500,700 to Urry. Pending patent applications in this area (both indicated to be allowable) are Ser. No. 533,670, now U.S. Pat. No. 4,605,413 directed to a chemotactic peptide and Ser. No. 533,524, now U.S. Pat. No. 4,589,882 directed to an enzymatically cross-linked polypeptide.

However, there continues to be a need for bioelastic materials based on the polypentapeptide and polytetrapeptide repeating sequences having modified chemical and biological characteristics.

SUMMARY OF THE INVENTION

Accordingly, it is an object of the present invention to provide a method of producing an elastomeric copolymer having a modulus of elasticity higher than that of the normal polytetrapeptide and polypentapeptide bioelastomers of the current series while retaining elasticity and biocompatibility.

It is also an object of this invention to provide an elastomeric copolymer having increased tensile strength over that available for normal polytetrapeptide and polypentapeptide bioelastomers.

These and other objects of the invention as will hereinafter become more readily apparent have been accomplished by providing a method of increasing the modulus of elasticity of a bioelastomer containing repeating units selected from the group consisting of elastomeric tetrapeptide and pentapeptide repeating units and mixtures thereof wherein said repeating units comprise amino acid residues selected from the group consisting of hydrophobic amino acid and glycine residues and wherein said repeating units exist in a conformation having a β-turn, which comprises:

chemically bonding a hexameric unit of the formula

—X—(APGVGV)$_n$—Y— wherein,

A is a peptide-forming of L-alanine;
P is a peptide-forming residue of L-proline;
G is a peptide-forming residue of glycine;
V is a peptide-forming residue of L-valine;
X is PGVGV, GVGV, VGV, GV, V, or a covalent bond;
Y is APGVG, APGV, APG, AP, A, or a covalent bond; and
n is an integer from 2 to 200, wherein said hexameric unit comprises at least 18 amino acid residues, into a polypeptide chain of said bioelastomer in an amount sufficient to increase the modulus of elasticity, tensile strength, or both modulus of elasticity and tensile strength of said bioelastomer.

DESCRIPTION OF THE PREFERRED EMBODIMENTS

The present invention arose as the result of investigations into the structure of elastic fibers present in blood vessel walls and other elastic materials, such as ligaments, present in humans and animals. The central portion of the elastic fibers of vascular wall, skin, lung and ligament contain a repeat hexapeptide (Ala-Pro-Gly-Val-Gly-Val)$_n$, a repeat pentapeptide (Val-Pro-Gly-Val-Gly)$_n$, and a repeat tetrapeptide (Val-Pro-Gly-Gly)$_n$, where Ala, Pro, Val and Gly respectively represent alanine, proline, valine and glycine amino acid residues. A high polymer of the hexapeptide has been synthesized, whereby it forms cellophane-like sheets. Other investigations have shown that the hexapeptide also exhibits chemotactic properties.

However, recent investigations have indicated that this natural hexapeptide and permutations of this sequence can be used to control the modulus of elasticity and tensile strength of artificial elastomers based on the polypenta- and polytetrapeptide sequences. As a result of this discovery, it has been found that elastic modulus and tensile strength of an artificial bioelastomer of the type described herein will be increased by chemically bonding a segment of the formula

wherein
A is a peptide-forming residue of L-alanine;
P is a peptide-forming residue of L-proline;
G is a peptide-forming residue of glycine:
V is a peptide-forming residue of L-valine:
X is PGVGV, GVGV, VGV, GV, V, or a covalent bond;
Y is APGVG, APGV, APG, AP, A, or a covalent bond; and
n is an integer from 2 to 200, wherein this "hexameric" segment contains at least 18 amino acid residues, into an elastomeric peptide chain. In this way the modulus of elasticity and tensile strength can be readily increased.

It will be noted that bioelastomeric polypeptide chains containing hexapeptide repeating units can be synthesized using any of the hexapeptide "monomers" that are permutations of the basic sequence. Thus, polymers generally will have the structure B$^1$-(hexapeptide repeating unit)$_n$-B$^2$ where B$^1$ and B$^2$ represent the remainder of a peptide chain which is discussed later in detail. In fact, if the peptide polymer is not synthesized using hexapeptide "monomers" but rather is synthesized by sequential adding of amino acids to a growing peptide (such as in an automatic peptide synthesizer) the designation of a repeating unit is somewhat arbitrary. For example, the peptide H-V(APGVGVAPGV-GVAPGVGVAPGVGV)A-OH can be considered to consist of any of the following repeating units and end groups: H-(VAPGVG)$_4$-VA-OH, H-V-(APGVGV)$_4$-A-OH, H-VA(PGVGVA)$_4$-OH, H-VAP-(GVGVAP)$_3$-GVGVA-OH, H-VAPG(VGVAPG)$_3$-VGVA-OH, or H-VAPGV-(GVAPGV)$_3$-GVA-OH.

Synthesis of the elasticity-modifying hexameric segment (which is incorporated into the final elastomeric peptide) is straight-forward and easily accomplished by a protein chemist. The resulting intermediate peptides generally have the structure B$^3$-(repeating unit)$_n$-B$^4$ where B$^3$ and B$^4$ represent any chemically compatible end group on the amino and carboxyl ends of the molecule, respectively, and n is an integer from 1 to about 200. When B$^3$ is H, B$^4$ is OH, and n=1, the compound is the hexapeptide itself. When n is greater than 1, the compound intermediate is a polyhexapeptide. It is possible that one or more amino acid residue or segment of amino acid residues not present in the normal hexapeptide sequence may be interspersed within a polyhexapeptide portion of an elastomeric polypeptide chain. As clearly indicated by the previous general formula and by the following discussion, the invention encompasses incorporation of a hexamer or polyhexapeptide into a larger peptide chain.

Other examples of terminal B$^3$ and B$^4$ end groups for the intermediate hexameric segment that is to be incorporated into the elastomeric polypeptide chain include portions of the repeating peptide units themselves with free amino or carboxylic acid groups or salts thereof, free amino or carboxylic acid groups or salts (especially alkali metal salts), and peptide or amino acid units that have retained a blocking group that was present during synthesis of the polypeptide or that have a biocompatible group added after formation of the polypeptide. Examples of blocking groups include t-butyloxycarbonyl, formyl, and acetyl for the amino end of the molecule and esters, such as methyl esters, as well as amides, such as the amides of ammonia and methyl amine, for the acid end of the molecule.

The first product obtained in the synthesis of a hexapeptide monomer that is typically produced in the process of preparing a hexapeptide segment is a protected hexapeptide, such as Boc-L·Val-L·Ala-L·Pro-Gly-L·Val-Gly-OBzl. This protected monomer is converted into a reactive monomer that can be incorporated into a peptide chain by, for example, replacement of the benzyl ester with the p-nitrophenyl ester, for example by effectively exchanging with p-nitrophenyl trifluoroacetate or bis-(p-nitrophenyl)carbonate, and removal of the Boc protecting group. The resulting reactive monomer is polymerized, in the presence of a base such as triethylamine or N-methylmorpholine as necessary, to give a polypeptide containing hexamer units. Copolymerization with a reactive penta- or tetrapeptide as described herein gives the final bioelastomer of controlled elasticity. Alternately, intermediate hexapeptide segments can be independently synthesized and incorporated into a block copolymer also containing elastomeric units as described below. A blocking group, such as H-Val-OMe may be added at the conclusion of the polymerization reaction to convert the remaining reactive p-nitrophenyl esters to non-reactive terminal groups if desired.

The elasticity-modifying hexapeptide segments are believed to operate much in the same way as the hard segments in segmented polyurethanes. For example, when polyhexapeptide, specifically (VAPGVG)$_n$, is dissolved in water at 4° C. and the temperature is raised, aggregation occurs over a relatively narrow temperature range and that range shifts to lower temperatures as the concentration is raised. The aggregation of the polyhexapeptide, in contrast to that of the polypentapeptide, is irreversible in water. The aggregates can be redissolved in trifluoroethanol-water mixtures and lyophilyzed to regain water solubility; i.e., the heat-illicited aggregation of the polyhexapeptide is not a true irreversible process. This is thought to be due to more rigid structure of the polyhexapeptide wherein on association there is an interlocking of hydrophobic ridges. Thus, in a copolymer comprising repeating hexapeptides and repeating pentapeptides, it appears that the hexapeptide repeats tend to associate selectively (i.e., to cluster) and that these clusters of stiffer hexapeptide units, separated by softer polypentapeptide or polytetrapeptide segments, impart additional rigidity to the composite material and result in an increased modulus of elasticity and increased tensile strength. This is quite analogous to the hard and soft segments of segmented polyurethanes, such as are described in Ulrich et al., in Synthetic Biomedical Polymers: Concepts and Applications, Szycher and Robinson, Eds. Technomic Publishing Co., Inc., West Port, Conn., 29-38 (1980).

Investigations have demonstrated that polyhexapeptide-polyhexapeptide interactions can occur within a predominantly polypentapeptide matrix. This is demonstrated by an increased elastic modulus which is consistent with a hard-segment role for the synthetic elastomeric polypeptide material. The results are also consistent with an interlocking by means of interdigitating hydrophobic ridges of repeating hexapeptide units. Preferred materials containing the hexameric segments of the invention would have the general formula $(E_m H_n)_p$, in which E represents an elastomeric tetrapeptide or pentapeptide unit and H represents a hexapeptide unit. Particularly preferred are polymers in which m is an integer from 1 to 100 (preferably 3 to 25), n is 3 or greater (preferably 5 to 10 and <m), and p is of such magnitude to provide a single polypeptide sequence having 50–5000 residues, preferably 500–200 residues (preferably p=10 to 100). It should be noted that the formula $(E_m H_n)_p$ does not necessarily represent a block copolymer, unless so specified, but can also represent a random copolymer having the indicated ratios of repeating units, wherein groups of at least three sequential hexamers are present in a random fashion. Typically, the ratio of elastomer unit to hexameric unit is from 1:1 to 10:1.

Biocompatibility tests have been conducted in rabbits on the polypentapeptide and on γ-irradiation crosslinked polypentapeptide. The material was found to be biocompatible and to be biodegradable. Because of the similarity of the polyhexapeptide sequences, a material incorporating hexapeptide sequences as described herein should have these same characteristics. Slow degradation is in fact a desirable property for many types of synthetic biocompatible materials. For vascular prosthesis, such a synthetic biomaterial can act as a temporary scaffolding on which new vascular wall is built. With elastomeric polypeptide biomaterials as described herein, there is the potential of beginning with a compliant vascular prosthesis which, taking advantage of the chemotactic nature of the hexapeptide units, would result in a restructured vascular wall with no identifiable foreign prosthetic material after the passage of sufficient time.

The amount of hexapeptide incorporated into a polypentapeptide or polytetrapeptide elastomer of the invention will naturally vary according to the desired modulus of elasticity and tensile strength. Incorporation of a small relative amount of the hexapeptide will result in a small increase in the elastic modulus and tensile strength while introduction of a larger proportion will result in a larger increase. Accordingly, the amount necessary to produce any increase in elastic modulus can readily be determined by simply experimentation. However, in order to retain sufficient elasticity of the resulting copolymer for biomedical applications, the ratios previous described are preferred.

The elastomeric units used with the hexapeptide segments to form the complete bioelastomer were described in the prior patents and patent applications described above in the section entitled Description of the Background, which are herein incorporated by reference. These applications describe elastomeric peptide units which can be utilized to form the elastomeric component of the present invention. An essential feature of the elastomeric pentapeptide, tetrapeptide, and D-amino-acid-containing tetra- and pentapeptide elastomeric units of the earlier inventions is the existence of a sequence of regularly recurring β-turns in the protein's secondary structure, i.e., the conformation of its peptide chain. A β-turn is characterized by a ten atom hydrogen bonded ring of the following formula:

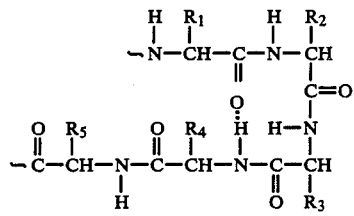

In this formula, $R_1$-$R_5$ represent the side groups of the respective amino acid residues.

The spiral structures produced by a series of β-turns are more open than the more common α-helix. As a result, the atoms between the atoms that participate in hydrogen bonding have a relatively greater freedom of movement, more so than in an α-helix. This is particularly true of librational motions involving peptide moieties. A libration is a torsional oscillation involving simultaneous rotational motions of the two single bonds on each side of a librating moiety. The moiety involved in a libration may be a single peptide bond or several peptide residues. For adequate freedom of motion to exist, it is important, however, that the carbonyl oxygen and the amino hydrogen of the peptide bond not be involved in a motional restricting hydrogen bonding to other parts of the molecule or to other peptide molecules. Otherwise a greater energy barrier to the libration exists and motion will be restricted. Since non-hydrogen-bonded segments having freedom of motion exist in the β-spiral between the points of hydrogen bonding for the β-turns, these segments may be said to be librationally suspended with librational capabilities. Librationally active suspended segments therefore are a structural feature that exists in the elastomeric polymer because of the repeating β-turns with relatively infrequent hydrogen bonding.

Another factor leading to the high librational freedom of such molecules is the absence of polar interactions between the amino acid residues, either intrachain or interchain, other than the previously mentioned hydrogen bond. The amino acid residues present are generally all hydrophobic or glycine and accordingly do not exert significant forces on one another through space. If charged or polar groups were present, electrostatic interactions would limit librational freedom and restrict the number of available states in the relaxed (non-extended) form of the molecules. Polar and charged amino acid residues are not strictly prohibited, however, if their presence does not destroy the elasticity of the polypeptide molecule as a whole. For example, an occasional serine residue is present in the polypentapeptide sequence of naturally occurring porcine tropoelastin without destroying elasticity. Accordingly, hydrophobic amino acid residues and glycine are preferred in forming elastomeric polypeptides of the present type although other amino acids may be present to a small extent.

The size of the repeating unit of the elastomeric component is important in determining the stability and dynamic properties of the $\beta$-spiral. Repeating units having fewer than four or more than five amino acid residues do not easily form $\beta$-spirals having the required librational motions. Three amino acid residues are too few for an efficient $\beta$-turn and six residues can result in intervening segments so long that other conformations become energetically more stable. Thus, elastomers of the present type appear to be limited to polypeptides having tetrapeptide or pentapeptide repeating units in the elastomeric component. Elastomers containing an amino acid residue of opposite chirality at position three, as disclosed in U.S. Pat. No. 4,500,700 and discussed briefly below, are also believed to be limited to polypentapeptides or polytetrapeptides, with polypentapeptides being particularly important.

Selective replacement of glycine residues at position 3 in the elastomeric repeating units with hydrophobic D-residues gives an elastomer having a higher modulus of elasticity. Studies of the dominant conformational feature of the polypentapeptide of elastin, the Type II $Pro_2$-$Gly_3$ $\beta$-turn previously discussed, indicate that a D-residue at position three will stabilize the $\beta$-turn. Substituting a D-amino acid residue for the Gly3 residue produces an elastomeric molecule (after cross-linking) having an elastic (Young's) modulus approximately twice that obtained for the corresponding molecule having a Gly3 residue.

When a repeating unit having an amino acid residue of opposite chirality is utilized, it is preferred that the amino acid residue in position three be a hydrophobic D-amino acid although other D-amino acids are also contemplated to be within the scope of the present invention. Amino acid residues having no more than 10 carbon atoms in their amino acid side chain are preferred. Preferred hydrophobic side chains are alkyl, aryl, and arylalkl, where aryl represents a phenyl or alkyl-substituted phenyl group. Particularly preferred are the residues of D-alanine, D-valine, D-leucine, D-isoleucine, D-phenylalanine, D-2aminobutanoic acid, and other molecules of similar size, polarity, and chirality. Especially preferred are alkyl side chains having 1-5 carbon atoms in an $\beta$-amino acid residue having an $\alpha$-hydrogen.

The choice of individual amino acids from which to synthesize the remaining sections of the elastomeric repeating units and resulting polypeptide is unrestricted so long as the resulting structure comprises librationally suspended segments in a $\beta$spiral. The amino acids are not restricted to $\alpha$-amino acids, although these are preferred, since it has recently become possible to predict the occurrence of $\beta$-turns from the $\alpha$-amino acid sequence of a polypeptide. A review article discussing the prediction of protein conformation, including the prediction of $\beta$-turns, was published by Chou and Fasman, *Ann. Rev. Biochem.*, 47, 251 (1978), which is herein incorporated by reference. The size of the side chains present in the hydrophobic amino acids does not greatly affect the $\beta$-spiral since the side chains generally extend outward from the surface of the spiral with some important but non-restrictive interturn hydrophobic interactions. However, in order to minimize interchain interactions, it is preferred that the side chain contain no more than 10 carbon atoms Preferred hydrophobic side chains are the same as those previously described for position three In addition, it appears from the studies leading to the present invention that preferred side chains of the amino acids are hydrogen or hydrocarbon chains having 1-4 carbon atoms. Examples of especially preferred residues are glycine and the naturally occuring L-amino acids alanine, valine, leucine, and isoleucine as well as closely related molecules such as 2-methyl-2-aminopropanoic acid, L-2-aminobutanoic acid, and L-2-methyl-2-aminobutanoic acid, although it is preferred that the $\alpha$-carbon have an $\alpha$-hydrogen. Proline is also a preferred amino acid.

Given positions of the repeating units of the elastomeric component have amino acid residues that are particularly preferred. The first amino acid residue is preferred to be valine, leucine, or isoleucine: the second is preferred to be proline; the third has been previously discussed; the fourth is preferred to be valine, leucine or isoleucine; and the fifth residue is preferred to be glycine.

An elastomeric component consisting entirely of repeating units in which the third amino acid residue is of opposite chirality, as described herein, has an elastic modulus approximately twice that of an otherwise identical polypeptide in which all the amino acids have the same chirality, such as those described in U.S. Pat. No. 4,187,852. Accordingly, it is possible to easily alter the elastic modulus by using a mixture of monomers and controlling the amount of crosslinking between adjacent peptide chains. Elastic modulus is proportional to the number of crosslinks, although not in a strictly linear fashion. It should be noted that the modification of elastic modulus described above by using amino acid residues of opposite chirality operates by an entirely different mechanism from that of the present invention. Furthermore, there is no indication of increased tensile strength for such earlier elastomers.

Because of the chirality of amino acids and of polypeptides produced therefrom, an equally effective polypeptide can be produced by using polypentapeptide repeating units in which all of the amino acids having chiral centers are of the opposite chirality from that previously described: i.e., L-amino acid residues are replaced with D-amino acids. Since both L- and D-amino acids are available commercially and can be used as starting materials in a synthesis of the polypeptide of the invention, for example in the method disclosed later, either of these species of the invention may be easily produced. However, since D-amino acids are relatively more expensive, the more preferred species is that in which all or most of the amino acid residues of the elastomeric component are derived from L-$\alpha$-amino acids and only the residue at position 3 is derived from a D-amino acid.

Methods of preparing elastomeric components in which the third position is occupied by a glycine residue have been disclosed in Rapaka and Urry, Int. J. Peptide Protein Res., 11, 97 (1978), Urry et al., Biochemistry, 13, 609 (1974), and Urry et al., J. Mol. Biol., 96, 101 (1975), which are herein incorporated by reference. The synthesis of these peptides is straightforward and can be easily modified to allow production of any polymer described in this application, if desired. The following summary, which is not to be considered limiting, is an example of one general method of synthesizing the polypeptides.

The first step in the formation of the elastomeric copolymer of the invention usually is synthesis of the various peptide monomers. Any of the classical methods of producing peptide molecules may be used in synthesizing the building blocks of the polymers of the present invention. For example, synthesis can be carried out by classical solution techniques starting from the C-terminal amino acid as a benzyl ester p-tosylate. Each successive amino acid is then coupled to the growing peptide chain by means of a water-soluble carbodiimide and 1-hydroxybenzotriazole. A typically used carbodiimide is 1-(3-dimethylamino-propyl)-3-ethylcarbodiimide hydrochloride (EDCI). During the coupling reaction the amino group is protected. The protecting group is then removed after condensation has taken place. A suitable protecting group is tert-butyloxycarbonyl (Boc), which can easily be removed by trifluoroacetic acid.

The structure, synthesis, and use of these elastomeric compounds and of various compositions containing these compounds is fully disclosed in the incorporated patent applications. The present invention is not related to these elastomeric components themselves but uses them in the formation of the total elastomeric material containing the hexameric segments.

Synthesis of the final elastomeric polyeptides containing the elastomer component and elasticity-modifying hexapeptide component of the present invention is straightforward and easily accomplished by a protein chemist. See, for example, the techniques described in Li and Yamashiro, J. Amer. Chem. Soc., 92, 7608–7609 (1970) which is herein incorporated by reference. The resulting generally polypeptides have the structure X-[(elastomeric unit)$_m$ (hexameric unit)$_n$]$_p$-Y where X and Y represent any chemically compatible end group on the amino and carboxyl ends of the molecule, respectively, and m, n, and p are as previously described. Block copolymers are preferred, although random copolymers are also suitable. Block copolymers can be synthesized sequentially in an automatic peptide synthesizer or by reacting preformed units consisting of activated elastomeric and hexapeptide units (which is preferred). If the latter method is used, it is preferred to use a shear stirring technique to orient the linear elastomeric units and to use EDCI as an activator. Relatively long reaction times and replenishment of EDCI during the course of reaction are preferred. Particularly preferred are polypeptides having molecular weights greater than 10,000 daltons, preferably up to 100,000 daltons. It is possible that one or more amino acid residue or segment of amino acid residues (such as the crosslinking segments later discussed) may be interspersed within the polypeptide chain so long as the elasticity and biocompatibility of the resulting molecule is not completely disrupted.

Examples of terminal end groups that can be present in bioelastomers of the invention include the repeating peptide units themselves with free amino or carboxylic acid groups or salts thereof and peptide or amino acid units that have retained a blocking group that was present during synthesis of the polypeptide or that have a blocking group added after formation of the polypeptide. Examples of blocking groups include t-butyloxycarbonyl, formyl, and acetyl for the amino end of the molecule and esters, such as methyl esters, as well as amides, such as the amides of ammonia and methyl amine, for the acid end of the molecule. The end groups are not critical and can be any organic or inorganic group that does not destroy the $\beta$-turn conformation of the elastomeric component and does not confer bioincompatibility to the molecule as a whole.

It is preferred that a bioelastomer containing elastomeric and hexapeptide repeating units be heated in order to kinetically drive the molecules to form hexamer-hexamer interaction. By heating the material, the hexamer segments are driven together in interlock as described above. When the products are cooled, insufficient kinetic energy exists to unlock the interlocked hexamer-hexamer segments.

The temperature to which the sample is raised in order to effect this heat treatment can readily be determined for a particular copolymer in at least two ways. First, elastic modulus can be measured as a function of temperature in a small sample of the copolymer product. There is a rapid increase in modulus of elasticity at the temperature at which the hexamer-hexamer interactions begin to occur. Alternatively, turbidity measurements (described in the experimental section) provide the same information. Opacity of the samples indicates interlocking of the hexamer regions.

The bioelastomers of the invention are quite stable to heat treatment. For example, a polypentapeptide (lacking the hexamers of the present invention) can be heated for 24 hours at 80° C. without degradation. The polyhexapeptide is even more stable to heat degradation. Bioelastomers of the invention can be autoclaved, thereby sterilizing the bioelastomer while providing the increased modulus of elasticity and tensile strength at the same time.

When bioelastomers of the invention are heat treated, it is preferred that this treatment take place prior to any of the cross-linking processes described later.

In addition to having an increased modulus of elasticity, bioelastomers of the invention also show an increased tensile strength and thus a greater resistance to tearing than bioelastomers prepared solely from the elastomeric units described in this specification.

An improved prosthetic material of higher tensile strength can be produced by using a collagen-like load bearing component in addition to an elastomeric component of the correct elastic modulus. This can be achieved by compounding the synthetic elastomeric high polymers described above to a second material with greater strength. The second material forms the core of the composite fiber and will be referred to as the "collagen analogue" or "core fiber". The term core fiber is not limited to those forms of elastomeric composite materials in which a first fiber is coated with a second material, but also refers to other forms in which a strength giving fiber (the core fiber) is chemically bonded to a second component that is elastomeric (the polypeptide) For example, elastomeric polypeptide fibers may form strands between the segments of a crimped core fiber. The essential feature is that a chemical bond (of any type) exists between the surface of the core fiber and the elastomeric polypeptide so that the two components do not become separated while the elastomeric component is being stretched or is reforming the relaxed $\beta$-spiral. The chemical bond may be covalent or ionic bonding, hydrogen bonding, or the result of electrostatic interactions of various types, such as ion-dipole and diopole-dipole interactions. Covalent bonding is preferred. Linkages may be formed in any conventional manner and, if covalent bonds are to be formed, they can be accomplished by reacting a functional group of the polypeptide with a functional group of the core fiber. The functional groups may be present naturally as part of the polypeptide or core fiber or may be formed later, for example, by suitable chemical reactions involving the already formed core fiber or polypeptide. Composite materials of this type are fully described in U.S. Pat. No. 4,474,851, which is herein incorporated by reference.

It is generally desirable to cross-link the molecules of the polypeptide prior to use in vivo in order to increase its strength and elasticity. If a composite fiber is being formed, it is preferred to perform the cross-linking after the polypeptide has adhered to the core fiber. The method of creating the linkage is not limited to the methods disclosed in this application and may be any method of covalent or non-covalent linkage that does not prevent the elastomeric copolymer or the composite fiber from behaving as an elastomer. Suitable methods and types of linkages include cross-linking with ionizing irradiation and chemical modification or substitution of amino acid residues of the peptide repeating units and of the collagen analogue repeating units in order to form reactive side groups that undergo chemical reaction with each other (chemical cross-linking) e.g., by amide linkage, aldol condensation, Schiff base formation, enzymatic cross-linking by lysyl oxidase, or ester formation. Another suitable method of cross-linking comprises the use of photoactivated agents such as those giving rise to carbenes or nitrenes which may be attached as amino acid side groups or introduced as separate diffusible molecules.

A preferred type of chemical cross-linking occurs when polypeptides are prepared in which some of the repeating units are replaced by units in which one of the amino acid residues is replaced by the residue of an amino acid that has a reactive side chain. Preferred is preparation of a first batch of polypeptide in which a residue of some of the repeating units is replaced by an amino dicarboxylic acid, such as aspartic or glutamic acid, and a second batch of polypeptide in which a residue of some of the repeating units is replaced by a diamino carboxylic acid, such as lysine or ornithine. After a mixture of these two batches has been formed into a sheath around the core fiber, the free amino and carboxylic acid side group are allowed to react to create the cross-linkages. Formation of cross-linked polypentapeptide produced in this manner is described in U.S. Pat. No. 4,187,852, which is herein incorporated by reference. If chemical cross-linking is used, it is also necessary to provide reactive functional groups in the core fiber so that linkages between the peptide elastomer and the core fiber will also occur. Such modifications are well understood by polymer chemists and may include, for example, glycidyl esters of acrylates or methacrylates (as examples of reactive groups present during formation of the core polymer), or amino or carboxylic acid groups added to the terephthalic acid moiety of Dacron (as examples of reactive groups formed after formation of the core fiber).

The degree of cross-linking is such that elastomeric properties are imparted to the resulting composite fiber and can be varied to provide the desired dynamic mechanical properties. Preferred is an average of one cross-link for every 5 to 100 elastomer repeating units with 10 to 50 being most preferred. The degree of chemical cross-linking can be controlled by selecting the proper proportions of reagents. In general, the ratio of repeating units with reactive side groups to unmodified repeating units within a single molecule can vary from 1:1 to 1:20 with a ratio of about 1:5 being preferred. When two batches of polypeptide containing carboxylate or amino side groups as described above are used, the ratio of carboxylate-side-group-containing polypeptide to amino-side-group-containing polypeptide can vary from 4:1 to 1:4 with a ratio of about 1:1 being preferred.

An additional method of chemical cross-linking using cross-linking units capable of being cross-linked by lysyl oxidase is described in U.S. Pat. No. application Ser. No. 533,524.

When irradiation cross-linking is performed, a satisfactory approach is irradiation with gamma radiation from a cobalt-60 source. Other radiation energies required to provide a cross-linking action without excessive destruction of the core fiber or elastomeric peptide structure may be easily determined by simple experimentation. The degree of cross-linking is determined by the length of time and energy of the irradiation when irradiation cross-linking is performed. At least two cross-linkages per molecule are needed. The number of cross-linkages per molecule and the elastic modulus increase as the radiation dose increases. The requisite time for any desired amount of cross-linking is easily determined by simple experimentation for any given source of irradiation energy. Samples of non-cross-linked polymer or composite fiber are exposed to the source of ionizing energy for varying lengths of time, and the resulting elastic modulus is measured. In this manner the irradiation time required to produce an elastic modulus necessary to match a specific design characteristic of the polymer or composite fiber can easily be determined. For use in forming vascular wall prosthetic devices, an elastic (Young's) modulus of $10^6$ to $10^7$ dynes/cm$^2$, preferably about $4 \times 10^6$ dynes/cm$^2$, for the cross-linked composite fiber is desired. This is approximately the elastic modulus of the vascular wall.

The elastomeric composite fibers may be woven into a fabric or an elastomeric fabric may be formed from a fabric of the core fiber material by coating and cross-linking the polypeptide on the surface of the fibers of the preformed fabric. When the resulting fabric has an elastic modulus of from $10^6$ to $10^7$ dynes/cm$^2$ and has been formed into an appropriate shape, for example, a tubular shape, resulting article may be used in vascular prosthesis. One simple way to obtain the desired tubular form, not considered to be limiting, would be to place the preformed woven and crimped tube of core fiber material between two concentric tubes (e.g., glass tubes) with the outer tube containing an aqueous solution of the elastomeric copolymer. The temperature of the solution would then be raised to allow coacervation to take place and the resulting impregnated woven fabric composition would be cross-linked by γ-irradiation at an appropriate dose.

It is also possible to form separate strength-giving and elastomeric fibers and to interweave them into a fabric of the desired shape. The first fiber, which is essentially non-elastic, would provide strength while the elastomeric polypeptide fiber would provide elasticity.

The type of prosthetic device which can be used in conjunction with the present invention is not limited. It is preferred, however, that the prosthetic device be one which is intended for incorporation into regenerating tissue, such as an artificial vein or artery or artificial skin. Two particularly preferred embodiments of the present invention involve using the chemotaxic polypeptide with a collagen/glycosaminoglycan composite material as an artificial skin, as described in U.S. Pat. No. 4,280,954, and with biocompatible artificial materials based on polypeptides as described in U.S. Pat. No. 4,187,852: U.S. patent application Ser. No. 308,091, now U.S. Pat. No. 4,474,851 filed Oct. 2, 1981; and U.S. patent application Ser. No. 452,801, now U.S. Pat. No. 4,500,700 filed Dec. 23, 1982, all of which are herein incorporated by reference. These are peptide-containing materials, and the chemotactic polypeptide may readily be attached by covalent bonding into such materials by the methods described above.

Once the synthetic composite material has been formed into an appropriate shape, if it is intended for use as a vascular replacement or patch, it is surgically inserted into a human or animal in place of diseased or missing vascular material. Tubular material may be used to replace an entire vein or artery by attaching each end to the distal and proximal free ends of a blood vessel having a missing or surgically removed section. Attachment is made so that blood flows through the tube without major leaking by any means capable of providing medically acceptable attachment, such as suturing or cauterizing. The elastomeric composite may be made in the form of a patch to be attached by the same methods if replacement of only a portion of a blood vessel is desired. Also tubular material may be used as a lining to replace diseased tunica intima following endarterectomy.

Other uses of the elastomeric material of this invention are also contemplated. The elastomer itself or the composite elastomeric fiber can be formed into sutures or used in the formation of artificial ligaments. As was previously described, the elastic modulus is easily controlled, resulting in a material having broad use, both in biological systems for replacement and repair of natural parts of an organism and in the myriad of nonbiological uses presently fulfilled by other elastomers. Thus any natural elastic system, especially those in which tropoelastin or elastin is naturally present, can be repaired by replacing a damaged portion of the system, such as a ligament, tendon, blood vessel wall, or the like, with an artificial elastomeric copolymer of the invention.

The elastomeric copolymers comprising elastomeric and hexapeptide components have generally the same elastomeric properties, except for modulus of elasticity and tensile strength, as previously described materials prepared from the elastomeric units and are useful for the same purposes.

The above disclosure generally describes the present invention. A more complete understanding can be obtained by reference to the following specific examples, which are provided herein for purposes of illustration only and are not intended to be limiting unless otherwise specified.

EXAMPLE

Abbreviations: BOc, tert-butyloxycarbonyl; Bzl, benzyl; DMSO, dimethylsulfoxide; EDCI, 1-(3-dimethylaminopropyl)-3-ethylcarbodiimide; HOBt, 1-hydroxybenzotriazole; IBCF, isobutylchloroformate: NMM, n-methyl morpholine; ONp, p-nitrophenylester; TFA, trifluoracetic acid; A, alanine; G, glycine; V, valine; P, proline; PPP, polypentapeptide (VPGVG)$_n$; PHP, polyhexapeptide (VAPGVG)$_n$ and P(HP)P, cosequential polyhexapentapeptide.

EXPERIMENTAL DETAILS

Peptide Synthesis

The synthesis of the sequential polypeptides of the hexapeptide sequence, Boc-(VAPGVG)$_n$-OCH$_3$ where n=2, 3, and 4 was carried out by classical solution methods as shown in Scheme I.

Scheme I
Synthesis of the Sequential Polypeptides of
the Hexamer Sequence

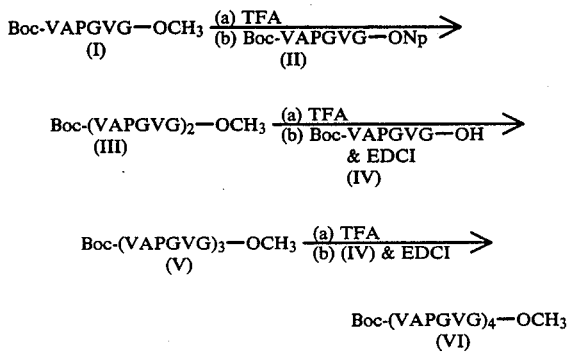

Boc-VAPGVG-OCH$_3$ (I) prepared as described in Urry et al., Int. J. Pept. Protein Res., 7, 367–378 (1975), was deblocked with TFA and coupled with Boc-VAPGVG-ON$_p$ (II) in the presence of HOBt to obtain Boc-(VAPGVG)$_2$-OCH$_3$ (III). After deblocking III, it was coupled with Boc-VAPGVG-OH (IV) using the water soluble carbodiimide, EDCI, to obtain the next higher homologue V. Similarly Boc-(VAPGVG)$_4$-OCH$_3$ (VI) was also obtained. The syntheses and purity of the oligohexapeptides with n=2 and 3 have been verified by C-13 NMR.

The synthesis of the polyhexapeptide, H-(VAPGVG)$_n$-V-OCH$_3$ has been carried out starting from the monomer sequence H-VAPGVG-ON$_p$. Recently, it was observed in the case of the preparation of the PPP, that with the permutation where Pro is present as the C-terminal amino acid in the monomer sequence, as H-GVGVP-ON$_p$ instead of H-VPGVG-ON$_p$, a very high molecular weight polymer (about 100,000 dalton) could be obtained Urry et al., in *Biocompatibility of Natural Tissues and Their Synthetic Analogues* (D. F. Williams, Ed.) CRC Press, Inc., Boca Raton, Fla., 89–116 (1985). Hence a Similar approach was taken for the preparation of the polyhexapeptide with Pro as the C-terminal amino acid in the monomer sequence. The synthesis of poly(GVGVAP)-OH is shown in Scheme II. The product may, of course, also be written H-GVG(VAPGVG)$_n$VAP-OH.

Scheme II
Synthesis of H—(GVGVAP)$_n$—OH

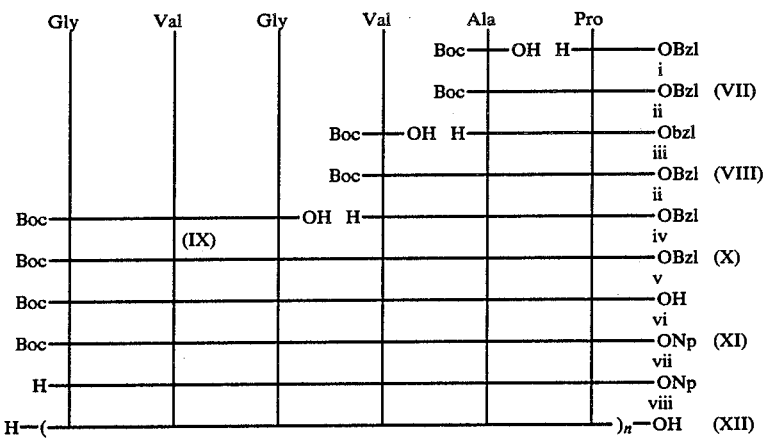

(i) IBCF—HOBt;
(ii) HCl/Dioxane;
(iii) IBCF;
(iv) EDCI—HOBt;
(v) H$_2$—Pd/C
(vi) Bis(p-nitrophenyl) carbonate;
(vii) TFA;
(viii) DMSO—NMM Boc-AP-OBzl (VII) was prepared by the mixed anhydride method in the presence of HOBt. After deblocking, the coupling was carried out with Boc-Val-OH to obtain the tripeptide benzyl ester (VIII) which was deblocked and coupled with Boc-GVG-OH (IX) to obtain the hexapeptide, X. Following hydrogenolysis, the peptide acid was converted to the p-nitrophenyl ester (XI) using bis(p-nitrophenyl) carbonate. After removal of the Boc group with TFA, a one-molar solution of the active ester in DMSO was polymerized for 14 days in the presence of 1.6 equiv. of NMM. On diluting with water the PHP was dialyzed against water, first using 3,500 molecular weight cut-off dialysis tubing for 7 days and then 50,000 M.Wt. cut-off tubing for 7 more days and finally the retentate was lyophilized.

Random copolymerization of hexa and pentapeptides: The active p-nitrophenylesters of the hexapeptide, H-GVGVAP-ONp, and the pentapeptide, H-GVGVP-ONp, were mixed in the desired ratio (1:2) and polymerized in the usual way. The product is a sequential polypeptide in which in a single chain there is presumably a random mixture of hexapeptides and pentapeptides in a 1:2 ratio. This product will be called a cosequential polyhexapentapeptide and will be abbreviated as P(HP)P. The purity of the intermediate and final compounds wa checked by thin layer chromatography, elemental analyses and nuclear magnetic resonance. Synthesis and purity of the polyhexapeptide, PHP, the cosequential polyhexapentapeptide, P(HP)P, and for comparison of the polypentapeptide, PPP, have been verified by C-13 NMR.

Temperature profiles of aggregation: Temperature profiles of aggregation (turbidity profiles) were obtained with a Cary 14 spectrophotometer set at 300 nm to follow light scattering as a function of increasing temperature. The heating rate was 30° C. per hour and to insure appropriate mixing of the polymers the sample cell was equipped with a 20 KHz vibrator. Samples were run in duplicate with fresh material used each time in a 1 mm rectangular cell with a total volume of 0.3 ml.

Reversibility of the polypeptides was checked immediately after each temperature run by exposing the sample to an ice bath for 30 minutes. If the aggregation was not reversible, the sample was further incubated at 4° C. for 16 hours. For the oligohexapeptides, reversibility was checked after the sample had been taken to 72° C. where n=3 and to 60° C. where n=4 and then when both had been taken to 80° C.

Preparation of polyhexapeptide sheet from trifluoroethanol: The polyhexapeptide (PHP) was evaporated from trifluoroethanol (TFE) in a round bottom flask after which ether was added and the resulting PHP sheet was removed. This material was cut into strips for the stress-strain studies.

Preparation of the $\gamma$-irradiation cross-linked elastomers: A quantity of 120 mg of dry sample wa placed in the bottom of a cryotube to which 204 $\mu$L of distilled water were added. The samples were allowed to hydrate at 4° C. to form a viscoelastic mass. In each tube a Plexiglas pestle was then inserted which had a 1 mm $\times$ 10 mm channel turned in it. As the pestle was inserted, the viscoelastic sample flowed into and filled the channel to form a continuous band with dimensions of 28 mm $\times$ 10 mm $\times$ 1 mm. The P(HP)P samples within the channel were held at 65° C. for 17 hours with slow rotation of the pestle. The samples were then placed in dry ice and taken to the $\gamma$-irradiation source. Irradiation cross-linking of the samples was carried out at the Auburn University Nuclear Science Center. The samples were placed at the center of a group of cobalt sources arranged in concentric circles. The configuration gives approximately 0.45 MRAD per hour gamma irradiation. The samples were exposed for 44.19 hours to give a total of 20 MRADs. The elastomeric bands are referred to as . for the cross-linked polypentapeptide, $X^{20}$-(PHP+PPP) for the cross-linked 1:2 mixture, respectively, of polyhexapeptide and polypentapeptide and $X^{20}$-P(HP)P for the cosequential polyhexapentapeptide with a random mixture of hexapeptide to pentapeptide (1:2) in the original polymerization.

Stress-strain studies: A strip of the polyhexapeptide sheet measuring 24 mm $\times$ 4.64 mm $\times$ 0.28 mm was clamped in the stress-strain apparatus with the distance between the grips being 10 mm. Elongation of the sample was done at a rate of 1.1 mm/min. The X-axis of the plotter recording the displacement of the moving grip was calibrated to 25.4 mm pen movement for a 0.1 mm grip displacement. The Statham UC-2 transducer with a UL4-2 load cell accessory used in our apparatus has a sensing element displacement of $2.15 \times 10^{-4}$ mm/gram of applied force. This correction was applied in calculating the elastic (Young's) modulus. The cross-section of each of the $\gamma$-irradiation crosslinked samples was measured prior to and after completion of each run. The elastic modulus of each sample was measured at 40° C. in water. The cross-linked cosequential polypeptide, $X^{20}$-P(HP)P, samples were then allowed to set for 12 hours at 65° C. and again the elastic modulus was measured at 40° C. The $X^{20}$-P(HP)P samples were subsequently swollen at 20° C. in water for five hours, heated at 80° C. in water for 17 hours and then the elastic moduli were again determined. During $\gamma$-irradiation cross-linking of some samples, vacuoles formed, the origin of which appeared to be the cryotube as no such quantity of vacuoles formed when using a glass container. When elastic moduli were determined no correction was made for the cross-sectional area of the vacuoles such that the elastic moduli are minimal values and can generally be considered to be about twice the value reported for the $X^{20}$-PPP and $X^{20}$-P(HP)P samples. The important element for the latter sample is the increase in elastic modulus on heat treatment at 65° C. and 80° C.

RESULTS

Aggregational Properties of Oligohexapeptides

When the hexapeptide (n=1) and the dodecapeptide (n=2) were examined, they exhibited little if any aggregation on raising the temperature to 80° C. When the octadecapeptide (n=3) was examined, however, it gave a temperature profile for turbidity with a midpoint just above 70° C., thereby demonstrating aggregation of polypeptide chains. On immediately lowering the temperature the aggregates redissolved, but if the temperature was raised to 80° C. and held there for a short period, the association in water did not reverse on standing overnight at 4° C. When the tetraeicosapeptide (n=4) was examined, the midpoint for the turbidity profile was shifted to a lower temperature, 57° C. This aggregation was found to be irreversible in water. Thus for the oligohexapeptides a repeating sequence of three to four hexapeptides is required before the polyhexapeptide-polyhexapeptide interaction is irreversible. To achieve irreversibility with heating at temperatures less than 80° C. an n of four is required.

The turbidity profiles for high molecular weight polyhexapeptide (n≃100) were determined. The polyhexapeptide-polyhexapeptide interaction was irreversible in water, and dissolution in trifluoroethanol and lyophilization with increasing amounts of water is required to again attain solubility in water at low temperatures. The turbidity profiles for a series of concentrations of high molecular weight polypentapeptide (n≃100) were also determined. Aggregation was immediately reversible on lowering the temperature. In an initial test as to whether hexapeptide sequences might function in an interlocking role when randomly interspersed in a polypeptide chain comprised of mostly pentapeptide, the random cosequential polyhexapentapeptide, P(HP)P, was prepared as outlined in the Experimental Section. The turbidity profiles for P(HP)P as a function of concentration were also determined. The aggregates, formed by heating this random copolymer of hexapeptide and pentapeptide with a ratio of 1:2, respectively, immediately redissolved on lowering the temperature below 25° C. If there are in the P(HP)P sufficiently long runs of uninterrupted repeating hexapeptides to effect some interlocking at elevated temperatures, these associations are separated by the hydration (swelling) of pentamer sequences on lowering the temperature. Whether such associations might be present at 40° C. can be tested in the cross-linked samples by the stress-strain studies reported below.

When a lower molecular weight polyhexapeptide with n≃40 is placed in one chamber of a tandem cell and polypentapeptide in the other, delayed turbitity was seen as the temperature was increased. The delayed turbidity change is believed to be due to aggregation of the lower molecular weight polyhexapeptide. On mixing the separately aggregated PHP and PPP, the PHP aggregation is not reversed on standing at 4° C. for more than 12 hours. If however the lower molecular weight PHP and the PPP are mixed at low temperature as solutions, on immediately lowering the temperature all aggregates redissolve. This indicates that there is significant PHP-PPP association on raising the temperature. When higher molecular weight PHP (n≃100) and PPP (n≃100) are combined as solutions at low temperature, a mixed aggregation is seen. This mixed aggregation does not redissolve on standing at 4° C. for several days. This demonstrates that there also can occur sufficient PHP-PHP interaction in the presence of PPP to achieve irreversibility i.e. interlocking.

Stress-Strain Studies

With 20 MRAD $\gamma$-irradiation of polypentapeptide carried out in the same manner as with the hexapeptide containing samples, the elastic modulus of the cross-linked polypentapeptide, $X^{20}$-PPP, A was in the range of 2 to $3 \times 10^5$ dynes/cm$^2$ with the measurement taking place in water at 40° C. A stress-strain curve can be used to compare polypeptides modified to contain hexamer units. As a reference for the cellophane-like polyhexapeptide, a sheet of PHP was cast from a high concentration in trifluoroethanol. The elastic modulus of this strip was found to be $7 \times 10^9$ dynes/cm$^2$. A representative sample of cosequential polyhexapentapeptide, cross-linked by 20 MRAD $\gamma$-irradiation i.e. $X^{20}$-P(HP)P, gave an additional value of $2.2 \times 10^5$ dynes/cm$^2$. On heating in water at 65° C. for 12 hours and re-examining at 40° C. in water, the elastic modulus had increased to $4.2 \times 10^5$ dynes/cm$^2$. The sample was then kept at 20° C. in water for 5 hours and then heated at 80° C. for 17 hours. The resulting elastic modulus at 40° C. in water had decreased to $3.3 \times 10^5$ dynes/cm$^2$. Averaged values for three samples were $1.9 \times 10^5$ dynes/cm$^2$, $4.2 \times 10^5$ dynes/cm$^2$ and $3.4 \times 10^5$ dynes/cm$^2$; these are for the initial values, the value after heat treatment at 65° C. and the value after heating at 80° C., respectively. The rationale for the choice of temperatures for the heat treatments derives from the turbidity profiles for the oligohexapeptides. A temperature of 65° C. resulted in irreversible association of oligohexapeptides with n=4. It would appear from the near doubling of elastic modulus on heating at 65° C. that some association of hexapeptide units did occur which functioned like additional cross-links. Irreversible association of oligohexapeptides with n=3 did not occur until 80° C. but association of P(HP)P was completely reversed on going below 25° C. (see results of aggregation studies above). On this basis the $X^{20}$-P(HP)P, that had been heated at 65° C., was allowed to swell at 20° C. for 5 hours. In analogy to the reversible aggregation of P(HP)P, this is expected to reverse all hexapeptide-hexapeptide interactions. The samples were then heated at 80° C. to see if additional putative (hexapeptide)$_n$-(hexapeptide)$_n$ associations might occur. This treatment caused a decrease in elastic modulus from what had been obtained after 65° C. treatment. While association of repeating hexapeptides with n=3 could possibly have been achieved, it is known that holding the temperature of PPP coacervate at 80° C. results in a very slow destructuring of the β-turns in the polypentapeptide. This and even the heat destructuring of the conformations of hexapeptide repeats within the cosequential polypeptide are possible explanations of the decrease in elastic modulus resulting from the 80° C. treatment.

Mixing polyhexapeptide with polypentapeptide in a 1:2 ratio produced polymers which were codissolved in a minimal amount of water (about 60% by weight) at 4° C. in the cryotube. The pestle was then inserted causing the viscoelastic solution to flow into the channel turned in the pestle. The pestle was rotated with the sample in an ice bath for several hours and the sample was then placed in dry ice until γ-irradiation at 20 MRAD. The product can he referred to as $X^{20}$-(PHP+PPP). The resulting band of material affords a stress-strain curve. The elastic modulus at between 50 to 60% extension was $2.6 \times 10^6$ dynes/cm$^2$. This value is essentially identical to that of natural fibrous elastin which similarly exhibits a lower initial slope. There is a marked reproducible hysteresis which is a result of the slow rate of retraction of the sample. The rate of change in length was approximately 1 mm/min.

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States is:

1. A method of increasing the modulus of elasticity of a bioelastomer containing repeating units selected from the group consisting of elastomeric tetrapeptide and pentapeptide repeating units and mixtures thereof wherein said repeating units comprise amino acid residues selected from the group consisting of hydrophobic amino acid and glycine residues and wherein said repeating units exist in a conformation having a β-turn, which comprises:

chemically bonding a hexapeptide unit of the formula

—X—(APGVGV)$_n$—Y— wherein
A is a peptide-forming residue of L-alanine;
P is a peptide-forming residue of L-proline;
G is a peptide-forming residue of glycine;
V is a peptide-forming residue of L-valine;
X is PGVGV, GVGV, VGV, GV, V, or a covalent bond;
Y is APGVG, APGV, APG, AP, A, or a covalent bond; and
n is an integer from 2 to 200, wherein said hexameric unit comprises at least 18 amino acid residues, into a polypeptide chain of said bioelastomer in an amount sufficient to increase the modulus of elasticity of said bioelastomer.

2. The method of Claim 1, wherein n is from 2 to 10.
3. The method of Claim 1, wherein n is about 5.
4. The method of Claim 1, wherein said chemical bonding comprises copolymerizing pentapeptide and hexapeptide monomers, tetrapeptide and hexapeptide monomers; or pentapeptide, tetrapeptide, and hexapeptide monomers, thereby form a random copolymer.
5. The method of claim 1, wherein said chemical bonding comprises forming a block copolymer of the formula $(E_mH_n)_p$ wherein E is a tetrapeptide or pentapeptide monomer, H is a hexapeptide monomer, m is an integer from 1 to 100, n is an integer greater than or equal to 3, and p is an integer from 10 to 100.
6. The method of Claim 5, wherein m is 3 to 25, n is 3 to 10, and p is 10 to 100.
7. The method of Claim 5, wherein the ratio of m to n is from 1:1 to 10:1.
8. The method of Claim 1, wherein said chemical bonding comprises cross-linking a first polymer comprising said pentapeptide or tetrapeptide repeating units or a mixture thereof with a second polymer comprising said hexameric repeating units.
9. The method of Claim 4, wherein said polymers contain an average of at least 500 amino acid residues.
10. The method of Claim 1, wherein said bioelastomer is heated after said incorporating, thereby interlocking said hexameric units in adjacent peptide chains.
11. A bioelastomer containing repeating units selected from the group consisting of elastomeric and pentapeptide repeating units and mixtures thereof wherein said repeating units comprise amino acid residues selected from the group consisting of hydrophobic amino acid and glycine residues and wherein said repeating units exist in a conformation having a β-turn, which is produced by:

chemically bonding a hexapeptide unit of the formula
—X—(APGVGV)$_n$—Y— wherein
A is a peptide-forming residue of L-alanine;
P is a peptide-forming residue of L-proline;
G is a peptide-forming residue of glycine;
V is a peptide-forming residue of L-valine;
X is PGVGV, GVGV, VGV, GV, V, or a covalent bond;
Y is APGVG, APGV, APG, AP, A, or a covalent bond; and
n is an integer from 2 to 200, wherein said hexameric unit comprises at least 18 amino acid residues, into a polypeptide chain of said bioelastomer in an amount sufficient to increase the modulus of elasticity of said bioelastomer.

12. The bioelastomer of Claim 11, wherein said bioelastomer comprises a copolymer of pentapeptide and hexapeptide monomers; tetrapeptide and hexapeptide monomers; or pentapeptide, tetrapeptide, and hexapeptide monomers.
13. The bioelastomer of Claim 11, wherein said bioelastomer comprises a block copolymer of the formula $(E_mH_n)_p$, wherein E is a tetrapeptide or pentapeptide monomer, H is a hexapeptide monomer, m is an integer from 1 to 100, n is an integer greater than or equal to 3, and p is an integer from 10 to 100.
14. The bioelastomer of Claim 13, wherein the ratio of m to n is from 1:1 to 10:1.

* * * * *